(12) United States Patent
Flynn et al.

(10) Patent No.: US 9,710,610 B2
(45) Date of Patent: Jul. 18, 2017

(54) ENTERAL FEEDING PUMP WITH FLOW ADJUSTMENT

(75) Inventors: Daniel P. Flynn, Weldon Spring, MO (US); James M. Harr, Wentzville, MO (US); Joseph A. Hudson, O'Fallon, MO (US)

(73) Assignee: Covidien LP, Mansfield, MA (US)

( * ) Notice: Subject to any disclaimer, the term of this patent is extended or adjusted under 35 U.S.C. 154(b) by 904 days.

(21) Appl. No.: 13/557,335

(22) Filed: Jul. 25, 2012

(65) Prior Publication Data

US 2014/0031784 A1 Jan. 30, 2014

(51) Int. Cl.
*G06F 19/00* (2011.01)
*A61M 5/168* (2006.01)
*A61M 5/142* (2006.01)

(52) U.S. Cl.
CPC ......... *G06F 19/3468* (2013.01); *A61M 5/142* (2013.01); *A61M 5/168* (2013.01); *A61M 5/16813* (2013.01); *A61M 5/16877* (2013.01); *A61M 2005/14208* (2013.01); *G06F 19/3462* (2013.01)

(58) Field of Classification Search
CPC .. A61M 5/142; A61M 5/16813; A61M 5/168; A61M 5/16877; A61M 2005/14208; G06F 19/3468; G06F 19/3462; G06F 19/326
See application file for complete search history.

(56) References Cited

U.S. PATENT DOCUMENTS

| 4,108,575 A | 8/1978 | Schal |
|---|---|---|
| 4,256,437 A | 3/1981 | Brown |
| 4,460,355 A | 7/1984 | Layman |
| 4,613,325 A | 9/1986 | Abrams |
| 4,634,426 A | 1/1987 | Kamen |
| 4,755,172 A | 7/1988 | Baldwin |
| 4,976,590 A | 12/1990 | Baldwin |
| 4,976,687 A | 12/1990 | Martin |
| 5,024,347 A | 6/1991 | Baldwin |
| 5,181,910 A | 1/1993 | Scanlon |
| 5,201,711 A | 4/1993 | Pasqualucci et al. |
| 5,213,483 A | 5/1993 | Flaherty et al. |

(Continued)

OTHER PUBLICATIONS

International Search Report from corresponding PCT Application No. PCT/US2013/051183 dated Nov. 29, 2013, 6 pages.

(Continued)

*Primary Examiner* — Imani Hayman
*Assistant Examiner* — Nilay Shah
(74) *Attorney, Agent, or Firm* — Blaine A. Page, Esq.

(57) ABSTRACT

An enteral fluid delivery system includes a pump having a motor coupled to a rotor configured to accept a portion of a tubing of a feeding set. The motor drives the rotor, which compresses the tubing to deliver to a patient enteral fluid during a feeding cycle. The system includes a user interface that is operatively connected to a memory that stores a plurality of types of enteral fluids. The user interface enables a user to select at least one type of enteral fluid. The system also includes a processor that is operatively connected to the pump. The processor adjusts the flow rate of the pump to deliver the selected enteral fluid for delivery based on one or more characteristics of the feeding fluid such as the viscosity or the caloric content.

13 Claims, 8 Drawing Sheets

(56) References Cited

U.S. PATENT DOCUMENTS

| | | | |
|---|---|---|---|
| 5,312,334 A | 5/1994 | Hara et al. | |
| 5,389,078 A | 2/1995 | Zalesky et al. | |
| 5,395,320 A * | 3/1995 | Padda | A61M 5/14228 |
| | | | 128/DIG. 12 |
| 5,429,602 A | 7/1995 | Hauser | |
| 5,460,490 A | 10/1995 | Carr et al. | |
| 5,499,968 A | 3/1996 | Milijasevic et al. | |
| 5,514,102 A | 5/1996 | Winterer et al. | |
| 5,531,680 A | 7/1996 | Dumas et al. | |
| 5,562,615 A | 10/1996 | Nassif | |
| 5,586,872 A | 12/1996 | Skobelev et al. | |
| 5,630,711 A | 5/1997 | Luedtke et al. | |
| 5,658,250 A | 8/1997 | Blomquist et al. | |
| 5,681,285 A * | 10/1997 | Ford | A61M 5/172 |
| | | | 604/151 |
| 5,720,721 A | 2/1998 | Dumas et al. | |
| 5,755,563 A | 5/1998 | Clegg et al. | |
| 5,772,635 A | 6/1998 | Dastur et al. | |
| 5,807,321 A | 9/1998 | Stoker et al. | |
| 5,842,841 A | 12/1998 | Danby et al. | |
| 5,871,465 A | 2/1999 | Vasko | |
| 5,885,245 A | 3/1999 | Lynch et al. | |
| 5,993,422 A | 11/1999 | Schafer | |
| 6,019,582 A | 2/2000 | Green | |
| 6,142,752 A | 11/2000 | Akamatsu et al. | |
| 6,228,057 B1 | 5/2001 | Vasko | |
| 6,283,719 B1 | 9/2001 | Frantz et al. | |
| 6,436,072 B1 | 8/2002 | Kullas et al. | |
| 6,468,242 B1 | 10/2002 | Wilson et al. | |
| 6,523,414 B1 | 2/2003 | Malmstrom et al. | |
| 6,659,976 B2 | 12/2003 | Beck et al. | |
| 6,749,410 B1 | 6/2004 | Burch | |
| 6,752,779 B2 | 6/2004 | Paukovits et al. | |
| 6,758,655 B2 | 7/2004 | Sacher | |
| 6,768,425 B2 | 7/2004 | Flaherty et al. | |
| 6,790,198 B1 | 9/2004 | White et al. | |
| 6,852,094 B2 | 2/2005 | Beck et al. | |
| 6,997,905 B2 | 2/2006 | Gillespie, Jr. et al. | |
| 7,029,455 B2 | 4/2006 | Flaherty | |
| 7,070,575 B2 | 7/2006 | Beck et al. | |
| 7,092,796 B2 | 8/2006 | Vanderveen | |
| 7,092,797 B2 | 8/2006 | Gaines et al. | |
| 7,118,347 B2 | 10/2006 | Solgaard et al. | |
| 7,121,143 B2 | 10/2006 | Malmstrom et al. | |
| 7,356,382 B2 | 4/2008 | Vanderveen | |
| 7,396,512 B2 | 7/2008 | DiTrolio et al. | |
| 7,447,566 B2 | 11/2008 | Knauper et al. | |
| 7,462,170 B2 | 12/2008 | Fournie et al. | |
| 7,645,258 B2 | 1/2010 | White et al. | |
| 7,753,880 B2 | 7/2010 | Malackowski | |
| 7,753,881 B2 | 7/2010 | Fournie et al. | |
| 7,753,883 B2 | 7/2010 | Fournie et al. | |
| 7,771,386 B2 | 8/2010 | Eggers et al. | |
| 7,794,423 B2 | 9/2010 | Gaines et al. | |
| 7,927,304 B2 | 4/2011 | Hudson et al. | |
| 8,021,322 B1 * | 9/2011 | Francis | G06F 19/3468 |
| | | | 600/300 |
| 8,025,634 B1 | 9/2011 | Moubayed et al. | |
| 8,574,190 B2 | 11/2013 | Francis | |
| 2002/0169636 A1 | 11/2002 | Eggers et al. | |
| 2003/0078534 A1 | 4/2003 | Hochman et al. | |
| 2006/0073048 A1 | 4/2006 | Malackowski | |
| 2006/0278221 A1 | 12/2006 | Schermeier et al. | |
| 2008/0119822 A1 * | 5/2008 | Knauper | A61J 15/00 |
| | | | 604/516 |
| 2008/0139997 A1 | 6/2008 | Sacchetti | |
| 2009/0030366 A1 * | 1/2009 | Hochman | A61M 5/20 |
| | | | 604/67 |
| 2009/0171289 A1 | 7/2009 | Davis et al. | |
| 2009/0221986 A1 * | 9/2009 | Wang | A61M 5/16877 |
| | | | 604/503 |
| 2010/0280486 A1 | 11/2010 | Khair et al. | |
| 2011/0196291 A1 | 8/2011 | Vischer et al. | |
| 2011/0257576 A1 | 10/2011 | Simpson et al. | |
| 2012/0078196 A1 | 3/2012 | Fournie et al. | |
| 2012/0245554 A1 | 9/2012 | Kawamura | |
| 2013/0025357 A1 | 1/2013 | Noack et al. | |
| 2014/0031784 A1 | 1/2014 | Flynn et al. | |

OTHER PUBLICATIONS

Written Opinion for the International Search Report from corresponding PCT Application No. PCT/US2013/051183 dated Nov. 29, 2013, 7 pages.

Dietscher et al., "Accuracy of Enteral Pumps: In Vitro Performance," Journal of Parenteral and Enteral Nutrition, vol. 18, No. 4, 1994, pp. 359-361.

Serrano et al., "The Relationship Between the Viscosity of Enteral Nutrition Products and Delays or Interruptions in the Infusion Rate Selected," Nutr Hosp., vol. 9, No. 4, Jul.-Aug. 1994, pp. 257-261—abstract only.

Tepaske et al., "Clinically Relevant Differences in Accuracy of Enteral Nutrition Feeding Pump Systems," Journal of Parenteral and Enteral Nutrition, vol. 30, No. 4, 2006, pp. 339-343.

Patent Examination Report No. 2 dated Jan. 18, 2016 in related Australian Patent Application No. 2013293294, 3 pages.

Abbott Nutrition Corporate Website, Abbott—Companion Enteral Nutrition Pump, Oct. 24, 2008, http://abbottnutrition.com/ph/10-08-2009-11-16-46_35691%20Companion%20Operating%20Manual%202008.pdf, 13 pages.

Covidien Corporate Website, Covidien-Kangaroo ePump, Enteral Feeding Pump Frequently Asked Questions, 2009, http://www.kangarooepump.com/pagebuilder.aspx?webPageID=131038&topicID=131038, 3 pages.

Fresenius-Kabi Corporate Website, Fresenius-Kabi—Enteral Feeding Pumps, Apr. 2010, http://www.fresenius-kabi.com/2202.htm, 6 pages.

Moog Inc. Corporate Website, Moog Inc.—Enteral Feeding Pumps, 2009, http://www.moog.com/products/medical-pump-systems/enteral-feeding-pumps/enteralite-infinity/, 12 pages.

Ross Nutrition Corporate Website, Ross Nutrition—Flexiflo Quantum Enteral Pump, 2004, http://www.bristolhomeinfusion.com/images/docs/Quantum-ENGLISH-manual.pdf, 20 pages.

Preliminary Report on Patentability dated Sep. 10, 2014 in related International Application No. PCT/2013/051183, 22 pages.

Patent Examination Report No. 1 dated Oct. 2, 2015 in related Australian Patent Application No. 2013293294, 3 pages.

Canadian Examiner's Report dated Jan. 20, 2016 in related Application No. 2,879,745, 5 pages.

Office Action dated Jul. 29, 2016 in related Chinese Application No. 201380045836.7. 20 pages.

Patent Examination Report No. 3 dated May 2, 2016 in related Australian Application No. 2013293294, 5 pages.

Office Action dated May 2, 2016 in related Korean Application No. 10-2015-7004606, 8 pages.

Office Action dated Jan. 11, 2017 in related Canadian Application No. 2879745, 4 pages.

Office Action dated Nov. 30, 2016 in related Korean Application No. 10-2015-7004606, 5 pages.

Office Action dated Apr. 12, 2017 in related Chinese Application No. 201380045836.7, 23 pages.

* cited by examiner

ENTERAL FEEDING PUMP WITH FLOW ADJUSTMENT

FIELD

Aspects of the present invention generally relate to enteral feeding systems used to deliver enteral fluids to a patient and, particularly, to a feeding system with a peristaltic pump that provides a feeding rate for a feeding fluid based on at least one characteristic of the feeding fluid.

BACKGROUND

Administering fluids containing medicine or nutrition to a patient via a patient's nose, mouth, or abdomen are known. Fluids can be delivered to the patient by gravity flow or may involve utilizing a flow control apparatus, such as a peristaltic pump through a pump set at a controlled rate of delivery. The feeding apparatus for administering fluids to the patient typically has a housing that includes at least one motor operatively coupled to a mechanism that is engaged with a feeding set or pump set by progressively compressing a tubing of the feeding set to drive the fluid through the tubing at the controlled rate. In typical rotary peristaltic pumps, the motor is operatively connected to a shaft that rotatably drives a pump rotor. The rotating pump rotor engages the tubing of the feeding set, pinching off a portion of the tubing and pushing the feeding fluid forward of the pinch point, e.g., closer to the patient than to the source of the fluid, toward the patient. In this manner, a peristaltic action that is created by the rotation of the rotor drives fluid through the tubing. Such enteral feeding pumps deliver feeding fluids of differing formulation, each of which may have differing characteristics, such as any of viscosity, nutritional value, caloric content, and other characteristics, which may result in variations in flow behavior.

SUMMARY

One or more aspects of the invention pertain to feeding fluid flow accuracy. Some aspects of the present invention pertain to enteral feeding of a feeding fluid through a feeding set based one or more characteristics of the feeding fluid. Further aspects of the invention pertain to compensating or adjusting one or more pump operating parameters based on one or more feeding fluid characteristics.

Aspects of the present invention pertaining to fluid delivery systems can provide a user the ability to select a formula on an enteral feeding apparatus which can determine and adjust the flow rate of the feeding fluid to compensate for characteristics of the selected feeding fluid. Some particular aspects of the present invention can utilize the caloric content information of a feeding fluid to modify the feeding formula flow parameters. Further aspects of the invention can pertain to feeding apparatus that can monitor the nutrition delivered, for example, as calories, volume of fluid, for the user selected formula and automatically determine a suitable flow rate and adjust the flow rate to compensate for the viscosity of the fluid.

In accordance with one or more aspects of the invention, an enteral fluid delivery system can comprise a pump having a motor coupled to a rotor, the rotor being configured to accept a portion of a tubing. The motor is operatively coupled to drive the rotor which compresses the tubing to deliver to a patient the enteral fluid during a feeding cycle. The system can include a user interface that is operatively connected to a memory storing information regarding a plurality of types of enteral fluids; the user interface enables a user to select at least one type of enteral fluid. The system can include a processor operatively connected to the pump for adjusting the flow rate of the pump to deliver the selected enteral fluid for proper caloric delivery based on the viscosity or the caloric content of the selected enteral fluid. The processor can be further configured to determine a flow rate based on a viscosity of the enteral feeding fluid; the viscosity of the enteral feeding fluid can be at least one of a low viscosity of less than about 75 cP and a high viscosity of greater than or equal to about 75 cP.

In another aspect of the present invention, a computer readable medium having multiple instructions stored thereon that, when executed, determine a flow rate for an enteral fluid delivery system. The enteral fluid delivery system includes a user interface, a processor, and a pump. The processor is operatively connected to the pump, which is configured or operable to deliver the enteral fluid through a pump tubing during a feeding cycle. When the instructions of the computer readable medium are executed, the processor is directed to enable a user to select a type of enteral fluid, enable a user to select at least one of a plurality of data parameters describing an enteral fluid, and adjust a flow rate of the pump to deliver the enteral fluid for proper caloric delivery based on the user selecting between either an enteral fluid type or at least one of the data parameters.

A method for operating an enteral fluid delivery system also embodies aspects of the invention. The enteral fluid delivery system includes a user interface having a memory storing types of enteral fluid, a processor, and a pump. The processor interfaces with the memory, and is operatively connected to the pump that delivers the enteral fluid through a pump tube. The method includes selecting an enteral fluid from a plurality of types of enteral fluids stored in a memory, pumping the selected enteral fluid through the pump at a flow rate to deliver the proper caloric requirement to a patient during a feed cycle, and adjusting the flow rate of the pump to deliver the selected enteral fluid based on the viscosity of the enteral fluid.

One or more aspects of the invention pertain to an enteral fluid delivery system comprising a pump having a motor coupled to a rotor, the rotor configured to accept a portion of tubing, the motor driving the rotor to compress the tubing for delivering to a patient enteral fluid during a feeding cycle; a user interface operatively connected to a memory storing at least one characteristic representative of a plurality of types of enteral fluids, the user interface enabling a user to select an enteral feeding fluid; and a processor operatively connected to the pump, the processor being configured to provide a flow rate of the pump to deliver the selected enteral feeding fluid based on the at least one characteristic of the selected enteral feeding fluid. The processor can be further configured to adjust a selected feeding rate to provide the flow rate based on a viscosity of the selected enteral feeding fluid. The processor can be configured to provide the flow rate based on at least one of a low viscosity of less than about 75 cP and a high viscosity of greater than or equal to about 75 cP. The processor can be configured to increase the feeding rate and provide the flow rate for low viscosity enteral feeding fluid. The processor can be configured to adjust a selected feeding rate and provide the flow rate based on a patient's specific patient group, wherein the patient group comprises at least one of an infant and an elderly adult. The processor can be configured to adjust a selected feeding rate to provide the flow rate based on a caloric content of the selected enteral feeding fluid as the at least one characteristic. The processor can be configured to decrease the selected feeding rate for a high caloric content enteral feeding fluid having at least about 1500 cal/mL. The processor can be further configured to increase the selected feeding rate for a low caloric content enteral fluid having less than about 1500 cal/mL.

One or more aspects of the invention can be directed to a computer readable medium having a plurality of instructions stored thereon to determine a flow rate for an enteral fluid delivery system, wherein the enteral fluid delivery system can include a user interface, a processor, and a pump, wherein the pump can be operable to deliver enteral feeding fluid through a pump tubing during a feeding cycle, wherein the processor can be operatively connected to the pump, and wherein the instructions, when executed, direct the processor to perform the steps of enabling a user to select a type of enteral feeding fluid; retrieving at least one data parameter based on the selected type of enteral feeding fluid; and adjusting a flow rate the enteral feeding fluid based on the at least one of the data parameter. The at least one data parameter can be at least one of a viscosity, an osmolality, a digestibility, a caloric content, a protein content, a sugar content, a fat content, fiber content, a free water content, a carbohydrate content, a cholesterol content, an amino acid content, a vitamin content, a mineral content, a nitrogen content, a sodium content, a potassium content, a chloride content, a calcium content, a magnesium content, an electrolyte content, and a nutritional requirement. The computer readable medium of can further comprise an instruction directing the processor to adjust the flow rate based on a patient group, wherein the patient group includes at least one of an infant and an elderly adult. Retrieving the at least one data parameter can comprise retrieving a viscosity data parameter of the selected type of enteral feeding fluid, and wherein adjusting the flow rate of the enteral feeding fluid comprises adjusting a feeding rate based on the retrieved viscosity data parameter. Retrieving the at least one data parameter can comprise retrieving a caloric content data parameter of the selected type of enteral feeding fluid, and wherein adjusting the flow rate of the enteral feeding fluid comprises adjusting a feeding rate based on the retrieved caloric content data parameter. The pump can have a motor coupled to a rotor, the rotor configured to accept a portion of the pump tubing, the motor driving the rotor to compress the tubing for delivering to a user enteral feeding fluid during a feed cycle, and further comprising an instruction directing the processor to adjust the motor to vary the flow rate based on a caloric content of the enteral feeding fluid. The computer readable medium can further comprise an instruction directing the processor to initially determine a flow rate based on the selected retrieved data parameter and a selected feeding rate.

One or more aspects of the invention can be directed to a method for facilitating delivery of an enteral feeding fluid, comprising providing a user interface, providing a memory component capable of storing at least one characteristic of at least one enteral feeding fluid, and operatively coupling a processor to the user interface and the memory component; the processor can be configurable to retrieve the at least one characteristic from the memory component based on at least one user entry, and generate at least one output signal that energizes a pump motor to deliver the enteral feeding fluid to a patient to achieve a user-defined feeding rate based on the at least one characteristic. The at least one user entry can be an enteral feeding fluid type and the user-defined feeding rate, and wherein the at least one characteristic is based on one of a caloric content and a viscosity of the enteral feeding fluid type. The output signal can correspond to adjusting the user-defined feeding rate for an enteral feeding fluid having a viscosity of greater than about 75 cP. The method can further comprise providing instructions executable by the processor, wherein the instructions can direct the processor to prompt the user to select a type of enteral feeding fluid at the user interface. The method can further comprise providing instructions executable by the processor; the instructions can direct the processor to prompt the user to provide a feeding rate of the enteral feeding fluid at the user interface. The method can further comprise providing instructions executable by the processor; the instructions can direct the processor to generate the output signal that adjusts the flow rate for a patient type selected from the group consisting of an infant and an elderly adult. The method can further comprise providing instructions executable by the processor; the instructions can direct the processor to retrieve the at least one characteristic selected from the group consisting of viscosity, an osmolality, a digestibility, a caloric content, a protein content, a sugar content, a fat content, fiber content, a free water content, a carbohydrate content, a cholesterol content, an amino acid content, a vitamin content, a mineral content, a nitrogen content, a sodium content, a potassium content, a chloride content, a calcium content, a magnesium content, an electrolyte content, a flow rate, and a nutritional requirement.

Other features will be in part apparent and in part pointed out hereinafter. For instance, various features discussed below in relation to any of the illustrated embodiments of the present invention may be incorporated into any of the above-described aspects of the present invention, alone or in any combination.

This summary introduces some aspects of the present invention and does not disclose an exclusive or exhaustive listing.

Figure 1:
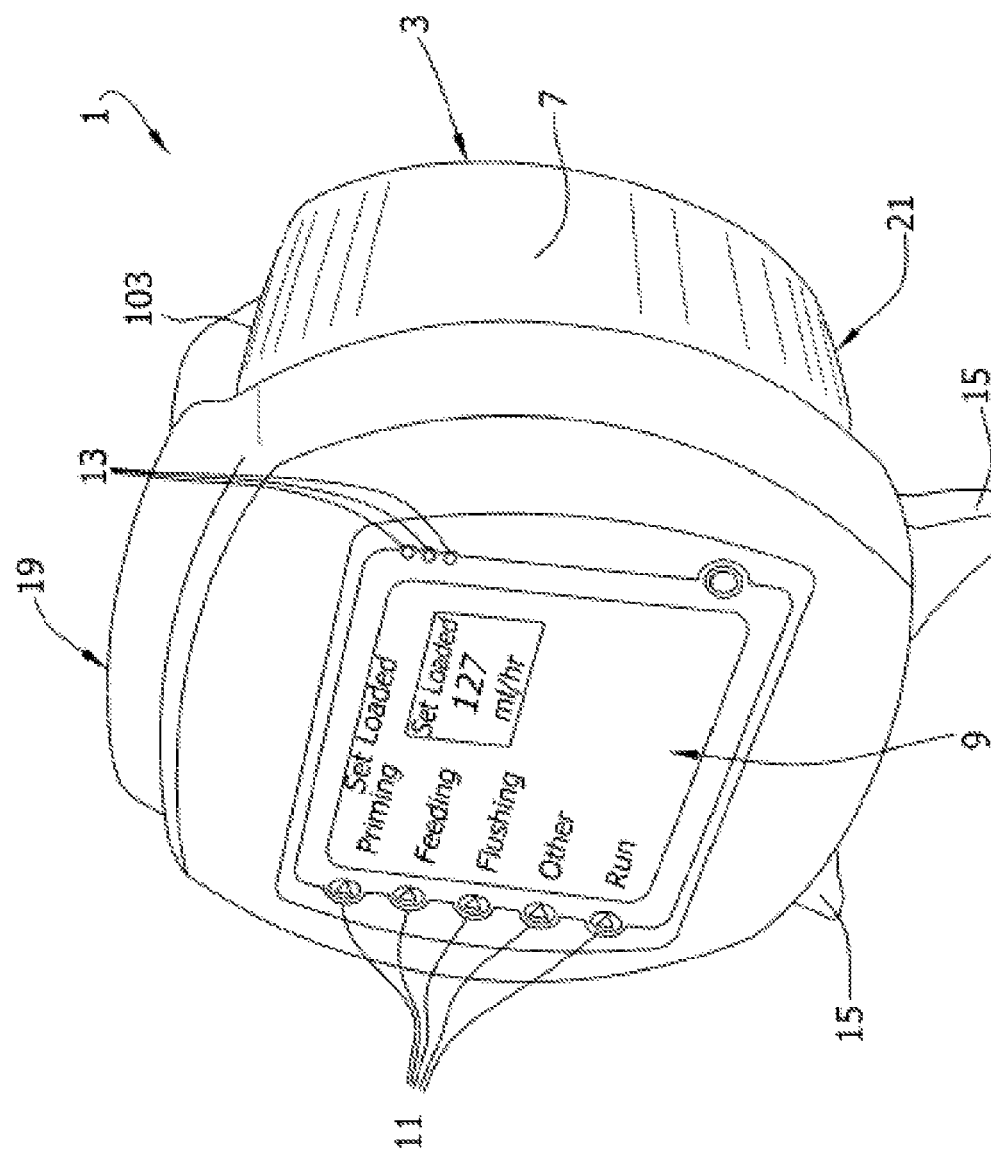
FIG. 1 is a schematic illustration showing a perspective view of a feeding apparatus, in accordance with one or more aspects of the invention.

In the drawings, which are not drawn to scale, like numerals may describe similar components in different views. Like numerals having different letter suffixes may represent different instances of similar components. The drawings illustrate generally, by way of example, but not by way of limitation, various embodiments discussed herein.

DETAILED DESCRIPTION

Figure 2:
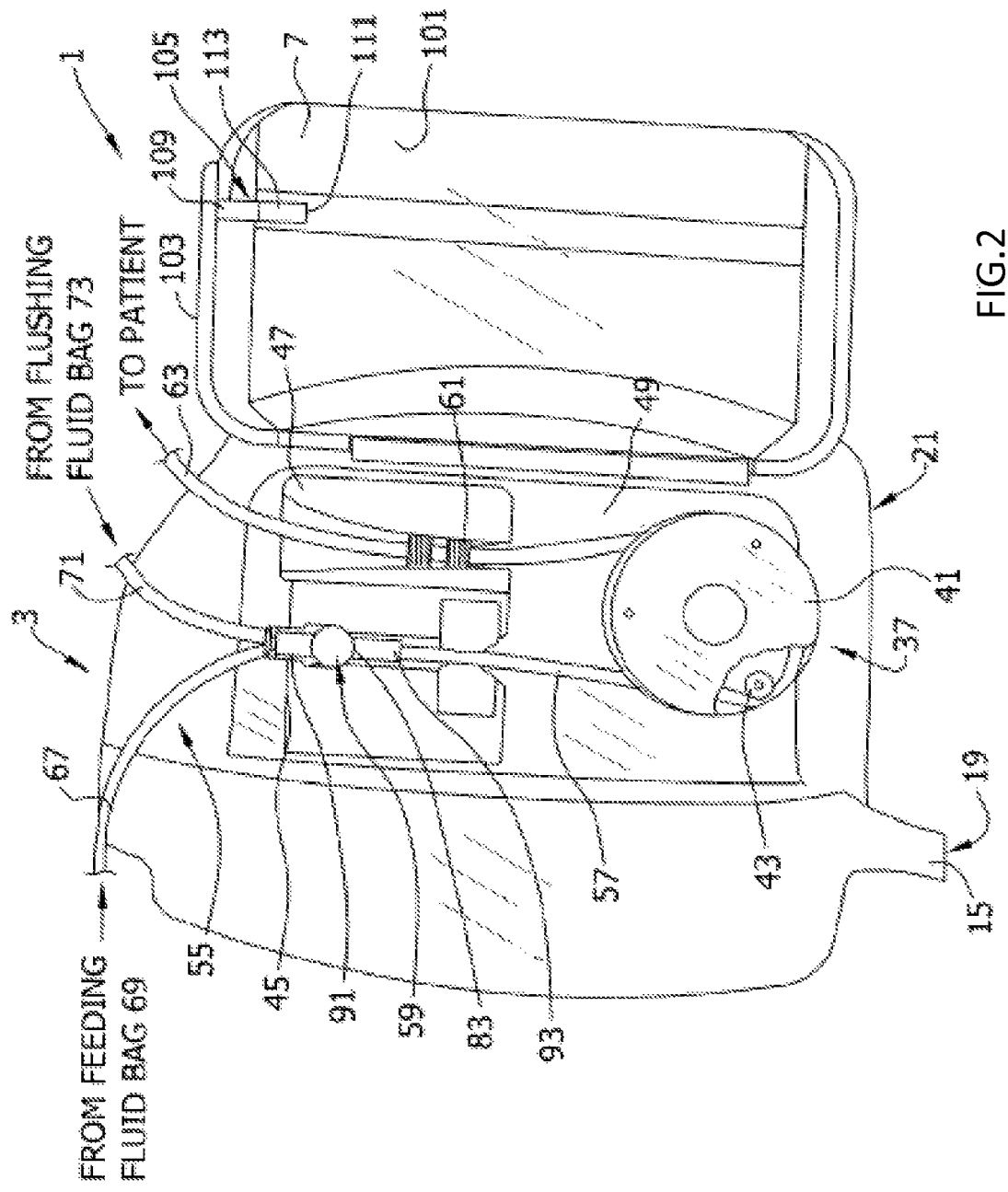
FIG. 2 is a schematic illustration showing an elevational view of a feeding apparatus with a fragmentary portion of a feeding set shown in FIG. 3, in accordance with one or more aspects of the invention.
Figure 3:
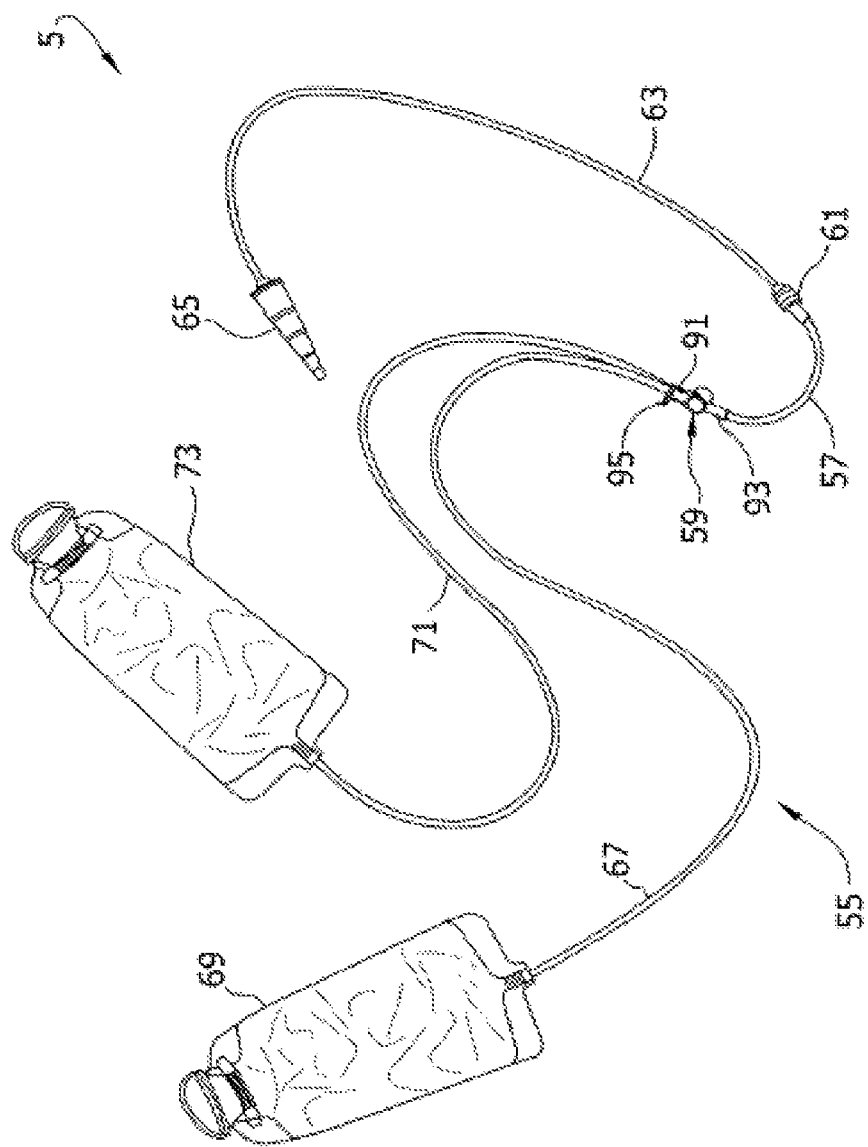
FIG. 3 is schematic illustration showing a perspective view of a feeding set that may be utilized in accordance with one or more aspects of the invention.

Referring now to the exemplary embodiments schematically illustrated in FIGS. 1-3, an enteral feeding pump or a flow control apparatus constructed according to the principles of the present invention is generally indicated at 1. The feeding pump 1 comprises a housing 3 that is constructed so as to allow mounting an administration feeding set 5 or feeding set or pump set. It will be appreciated that the term housing, as used herein, may include many forms of supporting structures including, without limitation, multipart structures and structures that do not enclose or house the working components of enteral feeding pump 1. The housing 3 includes a door 7 or closure that is pivotally connected or hinged thereto between a closed position (FIG. 1) and an open position (FIG. 2) which exposes a portion of the pump 1 that receives the administration feeding set 5. The pump 1 also has a user interface with a display screen generally indicated at 9 on the front of the housing 3 that is capable of displaying information about the status and operation of the pump. The pump 1 can further comprise buttons 11 and light emitting diodes 13 on housing 3 for use with the display screen 9 to facilitate exchanging information, such as providing and obtaining information, between the enteral feeding pump 1 and a user. The display screen 9 may be part of a front panel, generally indicated at 19, of the housing 3 attached to a main compartment 21 of the housing that holds at least a portion of the operating components of the pump 1. Various user interfaces for displaying information to the user and receiving user input may be implemented in accordance with one or more aspects of the invention. Any of the various configurations of the user interface can involve utilizing one or more graphical display subcomponents. As an example, the display screen 9 may be a graphical user interface having a touch screen by which the user can provide the input information. In other embodiments in accordance with the invention, the user interface can be a tethered component that can be used to provide input information, provide operating information pertaining to the flow control apparatus, or both. Optional legs 15 at the bottom front of the housing 3 support the flow control apparatus so that the display screen 9 is ergonomically positioned upwardly for viewing by an operator or user. In the exemplary description, the enteral feeding pump 1 is a rotary peristaltic enteral feeding pump; however, the present invention may be implemented in other types of pumps, including medical infusion pumps. The general construction and operation of the enteral feeding pump 1, except as set forth hereinafter, may be generally the same as disclosed in U.S. Pat. No. 7,927,304, the entire disclosure of which is incorporated by reference for all purposes. Moreover, although an administration feeding set 5 is shown, other types of pump sets (not shown) can be used within the scope of the present invention. The enteral feeding pump 1 typically further includes a pumping unit comprising a pump motor (not shown) located in the housing 3. The flow control apparatus can be connected to an external source of electrical power. Alternatively, or in addition, a battery may be disposed in the housing 3 for providing electrical power to the flow control apparatus. The pumping unit typically includes a pump rotor 37 mounted on a rotatable shaft (not shown) of the pumping unit. In one embodiment, the pump rotor 37 includes an inner disk, an outer disk 41, and preferably a plurality of rollers 43 (only one is shown) mounted between the inner and outer disks rotatable about their longitudinal axes relative to the disks. In the exemplarily illustrated embodiment, the pump motor, rotatable shaft and pump rotor 37 may broadly be considered a pumping device. The roller 43 engages the administration feeding set 5, which is also received in first and second chutes or recesses, designated 45 and 47, respectively, formed on a faceplate 49 of the pumping unit on which the pump motor is also mounted. The first and second chutes 45, 47 may broadly be considered as a receiving portion of the housing that receive portions of the administration feeding set 5 in a manner that will be described in more detail hereinafter.

The first chute or first lower recess 45 is disposed above the pump rotor 37 and the second recess 47 generally disposed adjacent the first lower recess 45. The housing 3 may have an upper recess (not shown) generally axially aligned with the first lower recess 45 and a shoulder (not shown) at the bottom of the upper recess for receiving and holding a portion of the pump set 5. Optionally, a curved recess (not shown) in the housing 3 above the second lower recess 47 can receive and hold another part of the pump set 5. The lower recesses 45, 47, optional upper recess and curved recess may be considered, individually or as a group, as a receiving portion of the housing 3 that receives parts of the pump set 5.

Referring now to FIG. 3, the administration feeding set 5 can comprise tubing indicated generally at 55 that provides a fluidic pathway between at least one source of fluid and a patient. Tubing 55 can be comprised of a medical grade, deformable silicone, and, as illustrated in FIG. 3, can comprise a first tube section 57 connected between a valve mechanism 59, and a mounting member 61. The feeding set 55 can comprise a second tube section 63 connected to the mounting member 61 and to a connector at an outlet thereof. The connector can be a barbed connector 65 or other connector configured to couple the set to a gastrostomy device (not shown) to be utilized with a patient. The feeding set 5 can further comprise a third tube section 67 that is connected or connectable at an inlet of the tubing 55 to a bag 69 containing feeding fluid and to the valve mechanism 59, and optionally a fourth tube section 71 that is connected or connectable at an inlet of the tubing 55 to a bag 73 containing flushing fluid and to the valve mechanism 59. The valve mechanism 59 can be turned to three positions. The valve mechanism 59 can be operable to selectively permit flow of feeding fluid from bag 69 or flushing fluid from bag 73, or prevent any fluid into the first tube section 57. A first position of the valve fluidly isolates the tube section 57 and prevents all fluid flow from any of the third and fourth tube sections 67, 71 to the first and second tube sections 57, 63; a second position of the valve fluidly connects the bag 69 to the tube section 57 and allows feeding fluid to flow from the bag 69 to the first and second tube sections 57, 63; and a third position of the valve fluidly connects the bag 73 to the first tubing section 57 and allows flushing fluid to flow from bag 73 to the first and second tube sections 57, 63. The feeding set 5 can include an upper sleeve 91, which is preferably disposed above the valve mechanism 59, and that receives the third and fourth tube sections 67, 71, and a lower sleeve 93, which is preferably disposed below the valve mechanism 59, and that receives the first tube section 57. The feeding set can further comprise a locating finger 95 that projects outwardly from the upper sleeve 91. The finger 95 can be an elongate structure that projects radially outwardly from the tubing 55 at a location adjacent the valve mechanism 59 of the feeding set 5. The locating finger 95 is typically attached to the tubing 55 of the feeding set 5 such that vertical movement of the locating finger causes corresponding vertical movement of the valve body 83 of the valve mechanism 59. In the illustrated embodiment, the valve body 83, upper sleeve 91, lower sleeve 93, and locating finger 95 are formed as unitary piece but in other configurations the locating finger may be separate from the valve mechanism and attached to another portion of the feeding set 5 in a suitable manner. The door 7 can have an inside surface 101, an upper surface 103, and a locating member 105 positioned on the inside surface and projecting outwardly therefrom. The locating member 105 can comprise a wedge-shaped structure near or proximate the upper surface 103. The locating member 105 can have a first generally vertical surface 109, a second generally horizontal surface 111, and a third angled surface 113 between the first and second surfaces. The door 7 is preferably pivotally mounted on the housing 3 for swinging movement between an open position (FIG. 2) allowing the feeding set 5 to be mounted on the pump 1 and a closed position (FIG. 1) covering the first chute 45 and the second chute 47. The locating member 105 is typically positioned on the door 7 to engage the locating finger 95 on the feeding set 5 when the door is moved to the closed position to secure the feeding set 5 in an operating position of the valve mechanism 59. The locating member 105 is typically positioned on the door 7 to engage the locating finger 95 on the feeding set 5 when the door is moved to the closed position to secure the feeding set 5 in an operating position relative to the valve mechanism 59.

The enteral feeding pump 1 can be configured to recognize what kind of set is installed and to alter or tailor its operation to conform to that called for by the particular kind of pump set. The enteral feeding pump 1 can be configured with sensors to detect whether the first tube section 57 is properly installed on the pump. The first tube section 57 is typically placed around the lower part of the pump rotor 37, and the first tube section 57 is typically substantially stretched around pump rotor 37. Examples of pump sets, including valve mechanisms, that may be utilized to implement one or more aspects of the invention are shown in U.S. Pat. Nos. 7,753,881 and 7,753,883, the entire disclosures of which are incorporated herein by reference for all purposes.

The flow rate for enteral feeding pump 1 can depend on the resistance of the tubes 63, 67 of pump set 5. As stated above, pump sets of different constructions can be used and various valve mechanisms can be used. Different combinations of pump sets and valve mechanisms can have different flow rates. In use, the feeding fluid bag 69 and flushing fluid bag 73 is typically suspended from a suitable support such as an IV pole (not shown). With the door 7 in the open position as shown in FIG. 2, the valve mechanism 59 can be placed in the first chute 45 in the operating position of the valve mechanism such that a valve shaft is received through an opening into the body 83 and is engageable with a valve stem of the valve mechanism 59. Rotation of the valve shaft selectively actuates the valve mechanism 59 into any one of the valve positions. The first tube section 57 is typically disposed around at least a portion of the rotor 37 and the mounting member 61 is typically disposed in the second chute 47. The second chute 47 can be generally funnel-shaped such as a frustoconically-shaped pocket so that the mounting member 61 can be placed into the chute 47 at a location in which the first tube section 57 is stretched around the portion of rotor 37. The first tube section 57 can relax and pull the mounting member 61 into the second chute 47. Preferably, the first tube section 57 is maintained in a stretched condition around the rotor when installed on the pump 1. The door 7 in the closed position covers the first and second chutes 45, 47 and the rotor 37. When the door 7 is closed and the valve mechanism 59 is loaded in the operating position, the horizontal surface 111 of the locating member 105 engages the locating finger 95 of the feeding set 5 to secure the feeding set in the operating position. The engagement of the locating member 105 with the locating finger can prevent or at least inhibit any upward pulling force on the feeding set 55 from dislodging the valve mechanism 59 from the operating position. The connector 65 at the end of the second tube section 63 can be connected to a conduit (not shown) attached to the patient. Other suitable connectors for facilitating delivery of the fluid may be used without departing from the scope of the present invention. The valve mechanism 59 preferably has a generally cylindrical valve body 83 having an opening (not shown) at the bottom of the valve body. The opening is typically shaped to receive a valve shaft (not shown) when the valve mechanism 59 is loaded on the pump 1. The valve mechanism 59 includes a rotatable valve stem (not shown) in the body 83 that defines a channel (not shown) that is configured and positioned to be aligned with the opening when the valve mechanism 59 is in the first, closed position. When the feeding set 5 is in an operating position on the pump 1, the valve mechanism 59 is on the pump such that the valve shaft is received in the channel and rotation of the valve shaft results in rotation of the valve mechanism. The pump 1 can actuate the valve mechanism 59 to any of the first, second, or third position by rotating the valve shaft based on the desired flow characteristics of the pump.

Figure 4:
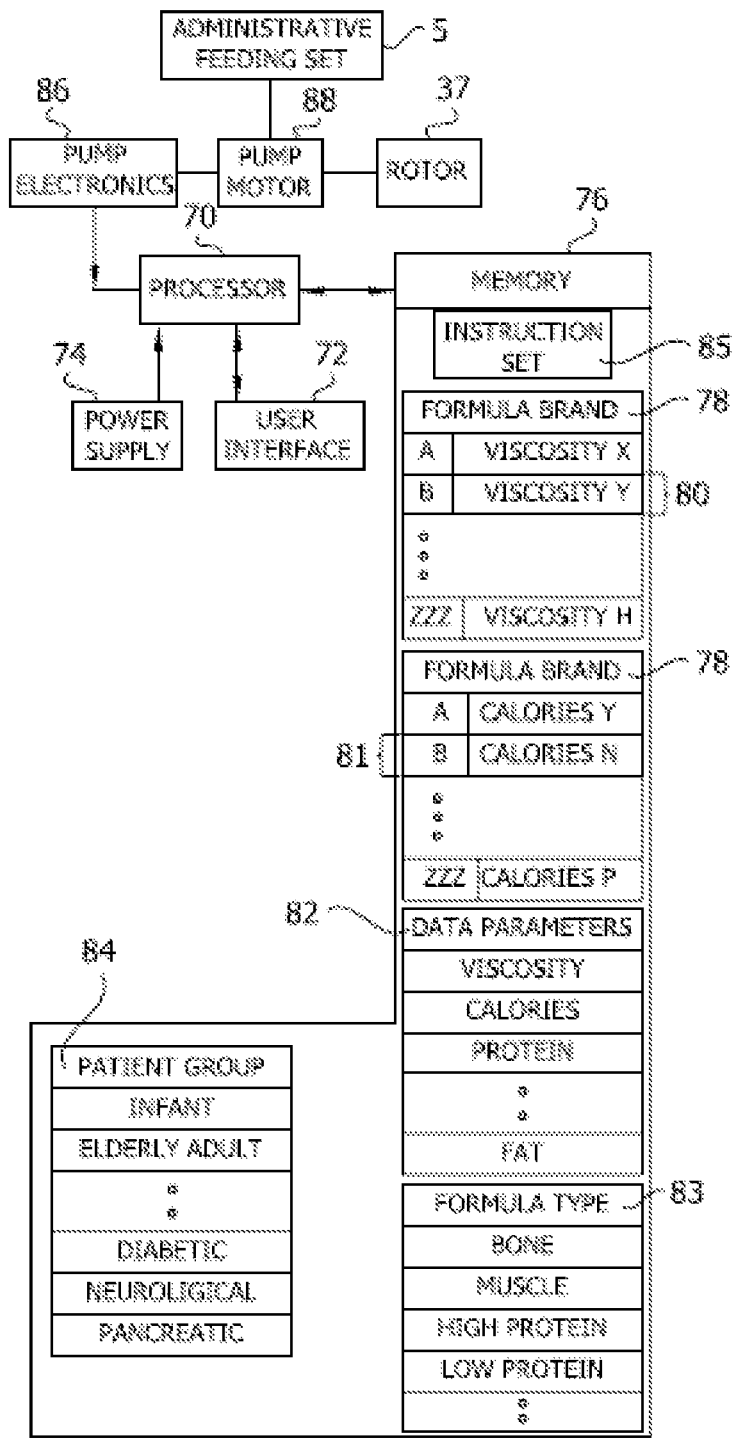
FIG. 4 is a block diagram showing representative functional components of an enteral feeding pump, in accordance with one or more aspects of the invention.

Referring now to FIG. 4, a block diagram exemplarily shows a system for selecting, compensating or adjusting the flow rate of the flow control apparatus according to one aspects of the invention. The flow control apparatus can have a processor 70 such as a microprocessor, or a microcontroller, that is operatively connected to a user interface, a memory 76, and a power supply 74 such as any of an internal power supply, e.g., a battery, and an external power supply, e.g., 110 VAC, that supplies electrical power to any one or more of the processor 70, user interface, and pump 1. Moreover, the processor 70 may comprise one or more discrete or distributed processing units.

Memory 76 can comprise one or more non-volatile memory components, e.g., ROM, PROM, EPROM, EEPROM, and flash memory. In other configurations, other types of non-volatile memory components can be utilized in addition to or instead of the non-volatile memory components such as but not limited to removable or portable data storage devices, such as hard disk drives, optical disk, magnetic tape, holographic memory, and memory cards. Alternatively or in addition, memory 76 can comprise one or more volatile memory components such as but not limited to random access memory (RAM), dynamic random access memory (DRAM), and static random access memory (SRAM).

In accordance with some aspects of the invention, memory 76 stores information pertaining to one or more characteristics of commercially available enteral fluids. For example, memory 76 can store, for any of a plurality of enteral formula brands or brand names 78, one or more characteristics, properties, and data parameters 82 associated with each of the plurality of brands such as, but not limited to, formula types 83. One or more embodiments in accordance with one or more aspects of the invention can involve utilizing brands of fluids, optionally with formulations thereof, and one or more corresponding characteristics and properties thereof such as, but not limited to, formula type, viscosity, caloric content, carbohydrate content, fat content, sugar content, digestibility, free water content, cholesterol content, osmolality, amino acid content, vitamin content, mineral content, nitrogen content, electrolyte content, and patient group type. The enteral formula brands 78 that may be pertinent to one or more embodiments of the invention, which are stored in memory 76, are generally commercially available in the marketplace under, for example, the marks ENSURE®, JEVITY®, and GLUCERNA®, manufactured by Abbott Laboratories, Chicago, Ill.; and ISOSOURCE®, manufactured by Nestle Nutrition, Vevey, Switzerland. In one embodiment, for example, memory 76 stores the names of the brands 78 and stores a corresponding formulation viscosity data 80 for each brand 78. In a further embodiment, memory 76 stores the names of brands 78 and stores a corresponding formulation caloric data 81 for each brand. In still a further embodiment, memory 76 also stores corresponding formulation protein content data. In yet a further embodiment, memory 76 also stores corresponding formulation carbohydrate content data. The flow control apparatus can thus provide or retrieve from memory 76, based on a selected brand, any one or more of corresponding associated patient group information, formula type information, osmolality information, digestibility information, sugar content information, fat content information, fiber content information, free water content information, carbohydrate content information, cholesterol content information, amino acid content information, vitamin content information, mineral content information, nitrogen content information, calcium content information, magnesium content information, and electrolyte content information, e.g., sodium content, potassium content, and chloride content. By having the commercially available enteral fluid brands 78 stored in memory 76 along with each brand's respective formulation information available for user selection, a user does not need to specify a viscosity, a caloric content, and other data parameters for a desired flow rate of the feeding fluid.

In accordance with still further aspects of the invention, the flow control apparatus can provide recommendations for an enteral fluid or brand based on one or more user requirements and information stored in memory 76, such as any of the multiple data parameters 82. For example, the user may provide one or more requirements as to any one or more of a viscosity, an osmolality, a digestibility, a caloric content, a protein content, a sugar content, a fat content, fiber content, a free water content, a carbohydrate content, a cholesterol content, an amino acid content, a vitamin content, a mineral content, a nitrogen content, a calcium content, a magnesium content, an electrolyte content, and a nutritional requirement, and the flow control apparatus can provide one or more recommendations of fluids as well as feeding recommendations that satisfy one or more of the user requirements.

In accordance with one or more further aspects of the invention, the flow control apparatus can utilize information pertinent to one or more formula types 83, stored in memory 76, to facilitate delivery thereof based on one or more desired characteristics. For example, the flow control apparatus may facilitate delivery of the fluid based on any one or more preferences or treatment protocols such as but not limited to higher calcium for bone growth and development, high protein content, low protein content, low fat content, lactose-free, gluten-free, and kosher, by providing fluid and feeding recommendations.

The flow control apparatus may facilitate delivery of a fluid by utilizing information stored in memory 76 based on patient groups 84 or patient requirement. The patient group 84 can include categories of types of patients such as an infant, e.g., a premature infant, a baby, a toddler, an elderly adult, a diabetic patient, a patient suffering from renal insufficiency, cardiac failure, pancreatic failure, neurological failure, e.g., central nervous system failure, head injuries, coma, hepatic failure, and multiple organ failure. Some aspects of the invention may thus provide recommendations based on types of patients each of which may require different formulations of enteral fluid and may require different flow rates as well as different durations of time for an enteral feeding. For example, the flow control apparatus may provide one or more feeding regimen for an infant that may not require as long a feeding duration and/or a slower feeding rate as an adult.

Figure 5:
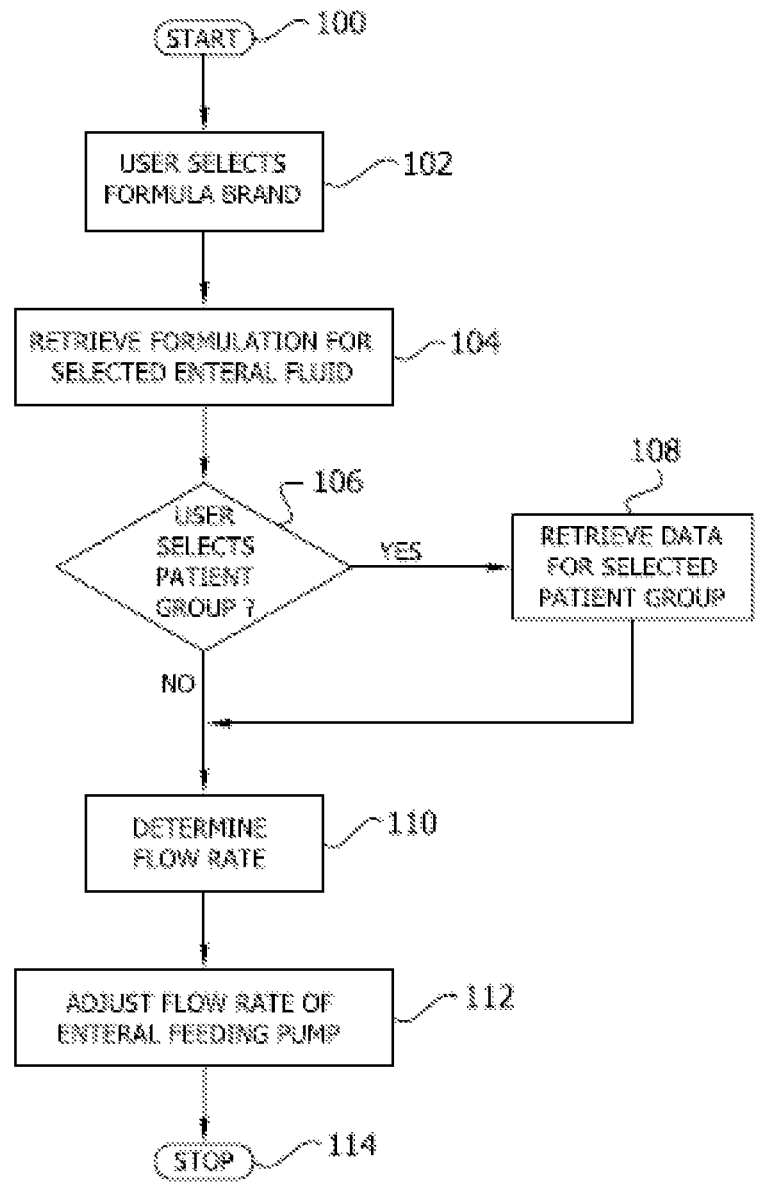
FIG. 5 is a flow chart illustrating a process of adjusting a flow rate of an enteral feeding apparatus, in accordance with one or more aspects of the invention.

Moreover, the memory 76 can further store a set of instructions 85, e.g., the instructions implement an algorithm that is described, for example, in FIG. 5, and when these instructions 85 are executed by processor 70, a flow rate is determined for the enteral feeding pump 1 based on the user selection of at least any one or more of a brand or brand name 78 with at least one or more data associated parameters such as but not limited to formula type, caloric intake requirement, fat intake requirement, protein intake requirement, mineral intake requirement, vitamin intake requirement, and patient group, and for a user-defined feeding rate.

The user interface accepts user input via, for example, buttons 11, and the user interface provides information to a user via display 9. In an embodiment, the display 9 can be a touch screen, as discussed above, to accept user input. The information shown on display 9 may include a series of screens (not shown) identifying, for example, the enteral formula brands 78, formula types 83, patient groups 84, and any of the one or more parameters available for user selection. For example, at the user interface 72, the user may enter specific formulation data 80, e.g., a particular viscosity, a particular caloric content, and at least one enteral formula brand 78 can be shown on display 9 for the user to select. The user can then select a particular brand from the displayed list.

In order to control the flow rate of enteral feeding pump 1, the processor 70 is operatively connected to a pump electronics 86, which, in turn, controls a pump motor 88. Pump electronics 86, for example, can comprise electrical components operatively coupled to energize the pump motor 88 at a particular rotational speed. The pump motor 88 is operatively connected to rotor 37, as shown in FIG. 1, and connected to the administrative feeding set 5, see FIG. 2 and as described above, to deliver enteral fluid to a patient at a target feeding rate. To determine the flow rate for a user-defined feeding rate of the enteral feeding pump 1 for the fluid to be delivered, the processor 70 retrieves from memory 76 the set of instructions 85 and retrieves one or more associated characteristics of the feeding fluid. Based on the user's selection, the processor 70 retrieves from memory 76 a formula brand 78, data parameters 82, formula type 83, and a patient group 84. If a formula brand 78 is selected by the user, the processor further retrieves the specific formulation 80 for the brand 78, and the user can be prompted to select one or more further characteristics. If a formula type 83, e.g., a formulation for high protein, a formulation for low protein, is selected by the user, the corresponding enteral fluid formulation is retrieved from memory 76. In another embodiment, if the user selects at least one or more data parameters 82, e.g., such as a viscosity, a caloric content, the processor 70 determines at least one or more formula brands to be displayed on display 9 for the user to select. The user can then select a particular brand from the available displayed list. The processor can then determine the flow rate of the feeding fluid for the predefined feeding rate utilizing the selected characteristic.

In addition to selecting a formula brand 78, at least one data parameter 82 and/or at least one formula type 83, the user can select a patient group 84. As stated above the patient group 84 includes categories of types of patients such as infants, elderly adults. These different types of patients can require different flow rates for an enteral feeding. Thus, the processor 70 acquires the required data from memory 76 associated with these types of patients. The user can then select a particular brand from the available displayed list.

The processor 70 retrieves the instruction set 85 from memory 76 and upon execution of the instruction set 85 determines a target or desired flow rate for the enteral feeding pump 1 based on a user selection of at least one of a formula brand 78, at least one data parameter 82, a formula type 83, and a patient group 84. The flow delivery can be adjusted or compensated for different formula characteristics and, therefore, the pump 1 can deliver the fluid at a target degree of accuracy. In one embodiment, the processor 70 utilizes viscosity information of the selected feeding fluid to modify a selected feeding rate of the feeding fluid selected in order to determine an operating flow rate for the enteral feeding pump 1. In an alternative embodiment, the processor 70 utilizes caloric information for the selected feeding fluid to modify a user-selected feeding rate in order to determine an operating flow rate for the flow control apparatus.

Upon determining the operating flow rate, processor 70 can send instructions that energize the motor to for provide the user-selected feeding rate, and optionally monitor the pumping parameters and intermittently, continuously, or continually adjust the instantaneous operating flow rate for enteral feeding pump 1 to achieve the target user-selected feeding rate. The processor 70 commands the pump electronics 86 to deliver the selected enteral fluid through the administrative feeding set 5 at the determined flow rate in order for the patient to receive the proper, predetermined, target, or desired caloric requirement during a feed cycle. The processor 70, also, can keep track of the volume of feeding or enteral fluid delivered to the patient, and the number of calories delivered to the patient. Other feeding parameters, such as but not limited to elapsed time, remaining time, and fat content delivered, may be monitored and optionally displayed through, for example, the user interface.

Referring to FIG. 5, a flow chart illustrates an exemplary method of determining a flow rate for the enteral feeding pump 1. At 100, the process begins by the processor 70 executing the instruction set 85 stored in memory 76. At 102, a user selects a formula brand 78 using the user interface. At 104, the processor 70 retrieves the formulation 80 for the selected formula brand 78 from memory 76. Alternatively, the processor 70 retrieves the formulation for a selected formula brand 78 based on viscosity. In another embodiment, the processor 70 retrieves the formulation for a selected formula brand 78 based on caloric content. At 106, the user can select a patient group 84. If the user selects a patient group, at 108 processor 70 retrieves data for the particular patient group selected and utilizes the information regarding, for example, an infant or an elderly adult to determine a target feeding rate and, preferably, a flow rate. Otherwise, at 110, the processor 70 determines a flow rate based on the selected formula brand 78 and the viscosity of the selected formula brand 78. Alternatively at 110, the processor 70 determines a flow rate based on the selected formula brand 78 and the caloric content of the selected formula brand 78. At 112, the processor 70 adjusts the flow rate of the enteral feeding pump 1 to, for example, achieve the target feeding rate. At 114, the controller terminates upon instruction from the user of upon delivering a user-defined volume of the feeding fluid to be delivered.

In an example, the flow control apparatus can prompt the user to select one of a plurality of enteral fluids to be delivered, typically via the user interface. The processor 70 retrieves corresponding information of the enteral fluid selected by the user via the user interface. Optionally, the user can further specify a feeding rate for the selected fluid. In response to the one or more selections, processor 70 can retrieve viscosity data for the selected enteral fluid from memory 76 and executes instructions to determine an appropriate flow rate based on the viscosity of the selected brand 78 and the target feeding rate. Optionally, the processor may continuously, continually, or periodically further modify the flow rate based on the retrieved viscosity information, for the target flow rate. The processor 70 can instruct the pump electronics 86 to deliver the enteral formula to the patient at the flow rate based on the viscosity of the enteral fluid.

In another example, processor 70 receives information representative of the enteral formula brand 78 selected by the user via the user interface. In response to the selection, processor 70 retrieves viscosity data for the selected brand from memory 76 and executes instructions to determine an appropriate flow rate adjustment based on the viscosity of the selected brand 78. The processor 70 instructs the pump electronics 86 to increase or decrease the flow rate based on the viscosity of the enteral fluid. For example, the flow rate will be increased for a low viscosity enteral fluid and decreased for a high viscosity enteral fluid.

Figure 6:
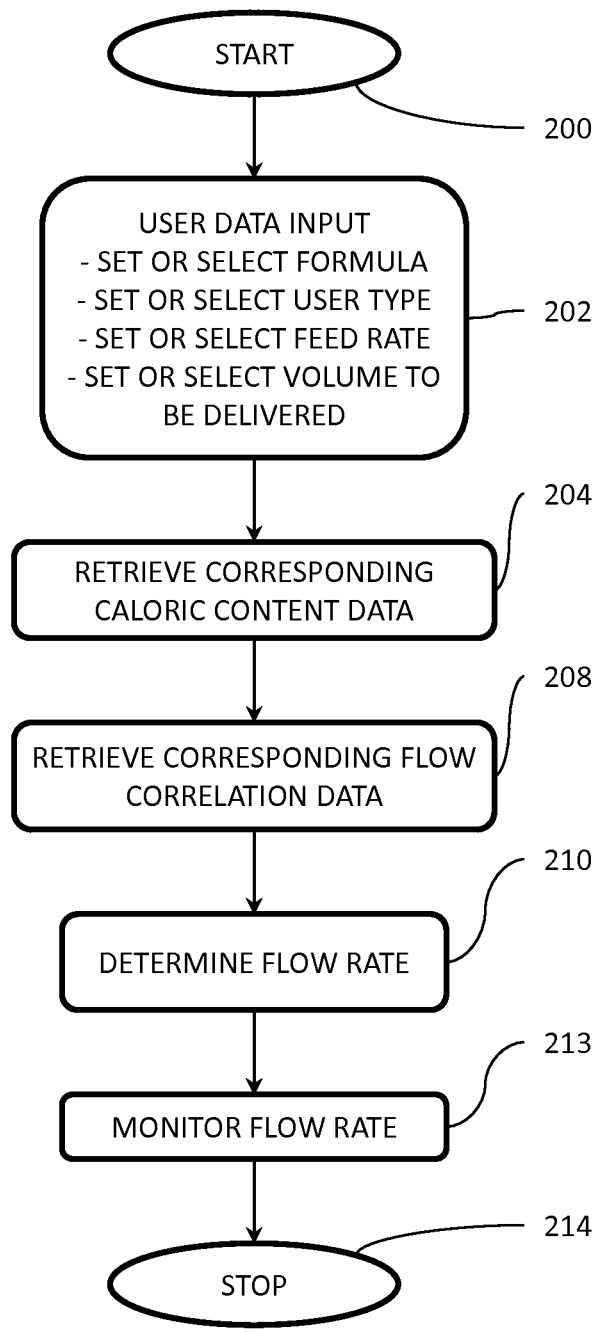
FIG. 6 is a flow chart illustrating a process of adjusting a flow rate of an enteral feeding apparatus, in accordance with one or more further aspects of the invention.

FIG. 6 shows a flow chart of another exemplary method of determining a flow rate for the flow control apparatus in accordance with one or more aspects of the invention. At 200, the feeding regimen can commence with the flow control apparatus available to receive feeding instructions or data. The controller of the apparatus can be configured to display at the user interface thereof, user prompts and user data inputs such as any one or more of the formula information, user type information, and feed rate information. At 202, the user can, for example, set or select from an available listing of formula or brands through the user interface, the particular feeding fluid to be administered and the flow control apparatus can then prompt the user to set or select a user-defined feed rate of the user-defined feeding fluid, a user-defined amount of the user-defined feeding fluid to be delivered, or both, through the user interface. Optionally the flow control apparatus can prompt the user to set or select the user type from an available listing of user types through the user interface. The controller of the flow control apparatus receives from the user interface any of the user-defined parameters and retrieve, at 204, a caloric content corresponding to the user-defined feeding fluid to be administered; and retrieve, at 208, a corresponding flow correlation data for the user-defined feeding fluid. The controller modifies, at 210, the user-defined feeding rate, based on the retrieved flow correlation data for the corresponding user-defined feeding fluid, to generate a modified flow rate, and sends instructions to energize the pumping unit to operate according to the modified flow rate. At 213, the controller monitors the actual flow rate and verifies progression of the feeding regimen to achieve the modified flow rate or the user-defined feeding rate or both. Optional display operations that may be performed contemporaneously, intermittently, or continuously during the feeding operation can be any one of the delivered volume of feeding fluid, the remaining volume of fluid to be delivered, and the amount of feeding time remaining for delivering the feeding fluid. At 214, at completion of the feeding, the controller de-energizes the pumping unit and terminates the feeding operation. Any of the delivered amount of feeding fluid, the delivered amount of calories can be determined by the controller, for a user-selected period, e.g., delivered to date, delivered for the week, or delivered for the month, and displayed at the user interface. Other optional information which the controller can determine and provide include, for example, any one or more of a log of feeding activities with or without associated date, time and duration of delivery, and average daily calories delivered on a weekly or monthly basis.

Powders, e.g., a protein powder, can be added to a commercially available enteral fluid to increase, for example, the protein content, the caloric content, the carbohydrate content. In some instances, medicines in tablet form may be crushed into a powder and added to an enteral fluid for easier delivery of the medicine to the patient. The addition of a powder may increase the viscosity of the fluid, and thereby affect the flow rate of the fluid. In such an instance, the amount of powder, e.g., grams or ounces, added to the enteral fluid is entered by the user via user interface. The processor 70 then may compensate for the change in viscosity by determining a flow rate based on the increased viscosity of the fluid because of the addition of the powder. The processor 70 can determine, based on the flow rate, for example, the number of calories that have been delivered to a patient and the duration of the delivery protocol. Feeding can stop once the programmed amount of enteral fluid has been delivered to the patient to prevent or reduce the likelihood of aspiration, gastroesophageal reflux, nausea, or have other undesirable complications.

Further aspects of the invention can involve modifying or retrofitting existing flow control apparatus to incorporate any one or more algorithms and associated components to effect providing a user interface to accommodate user-defined parameters and utilizing the user-defined parameter to retrieve corresponding correlation factors and achieve desired pumping or flow targets or requirements. Further aspects of the invention thus contemplate various computer-readable media as well as controller-accessible components storing instructions executable by one or more controllers or control systems that perform any one or more acts as exemplarily presented at FIGS. 5 and 6 and described herein. Still further aspects of the invention can be directed to computer-readable media or controller-accessible components including data structures that includes or incorporates any one or more of the relationships, such as those graphically illustrated at FIGS. 8A and 8B, between flow rate and user-defined parameters that facilitate realization of flow rate functionality modification.

The function and advantages of these and other embodiments of the invention can be further understood from the example below, which illustrates the benefits and/or advantages of the one or more systems and techniques of the invention but do not exemplify the full scope of the invention

EXAMPLE

Several feeding tests were conducted using commercially available enteral feeding fluids to determine the relationship relative to viscosity as well relative to the caloric content of the enteral feeding fluid and the actual flow rate. The feeding fluids utilized in this example included a control, tap water from Hazelwood, Mo. and the following feeding fluids, JEVITY® 1 CAL, JEVITY® 1.2 CAL, JEVITY® 1.5 CAL, PROMOTE® WITH FIBER, and TWOCAL® HN nutritional formulae available from Abbott Nutrition.

A Brookfield digital viscometer, model LVDE115, was used to measure viscosity.

The respective caloric content indicated on the container label for each fluid was utilized The various fluids were pumped for thirty minutes at ambient conditions, at about 23° C., collected in a collection cup, and the weight of each of the pumped fluids was measured. The volume of the pumped, delivered fluid was derived based on the respective specific gravity for each fluid.

KANGAROO JOEY™ pumps and anti-free flow (1000 mL) feeding sets (no. 763656), from Covidien, Mansfield, Mass., were utilized in each of the feeding tests. Each of the pumps was operated at a user-defined feeding rate for all fluids of 125 mL/hr.

For the viscosity study, three feeding sets/pumps were utilized to pump each of tap water, JEVITY® 1 CAL, PROMOTE® WITH FIBER, and TWOCAL® HN nutritional formulae. For the caloric content study, four feeding set/pumps were utilized to pump each of tap water, and JEVITY® 1 CAL, JEVITY® 1.2 CAL, JEVITY® 1.5 CAL, and TWOCAL® FIN nutritional formulae. In particular, pump 1 with feeding set 1 was used to pump tap water for a feeding duration of thirty minutes. The source bag was drained to empty current fluid, e.g., water, and a next enteral feeding fluid, e.g., JEVITY® 1 CAL, was charged into the source bag. The pump was operated to purge any previous fluid in the feeding set. The next feeding test was then commenced by operating the pump under similar conditions. Feeding tests were repeated using the same feeding set and pump for the other feeding fluids; two additional feeding sets/pumps were likewise utilized to perform the additional feeding tests in the viscosity study. The feeding tests to evaluate the caloric content relationship were similarly performed except that four feeding sets/pumps were used.

Figure 7A:
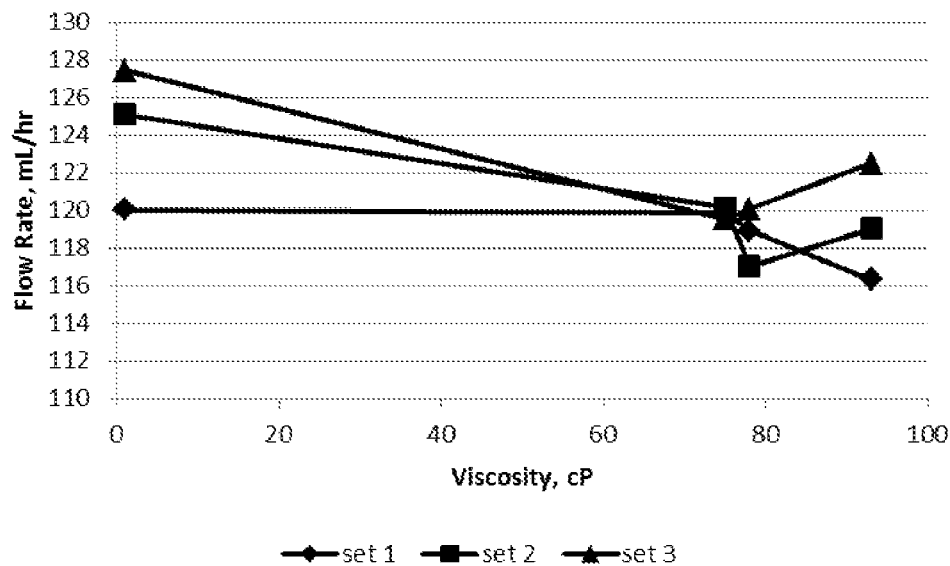
FIG. 7A is a graph illustrating a relationship between feeding fluid flow rate and viscosity for several commercially available feeding fluids, which may be utilized in accordance with one or more aspects of the invention.
Figure 7B:
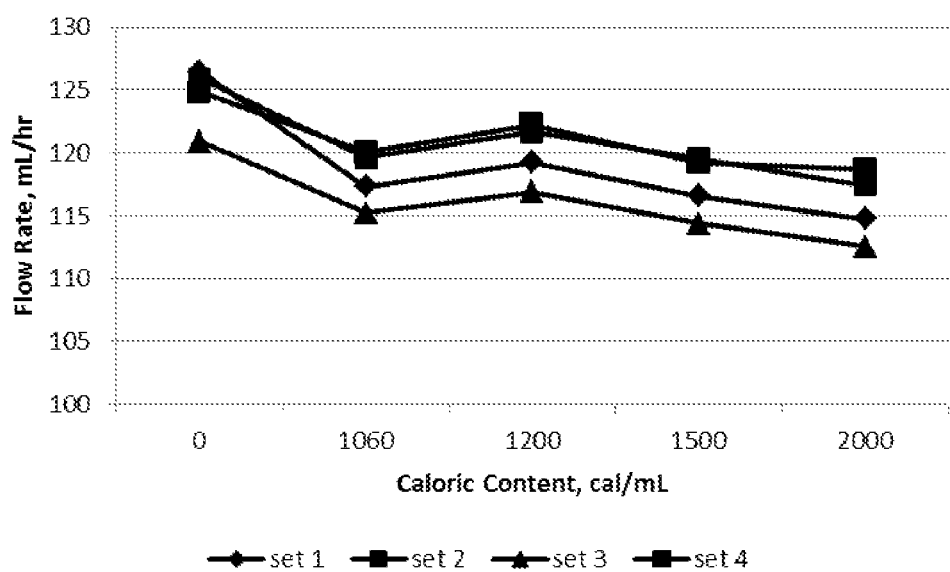
FIG. 7B is a graph illustrating a relationship between flow rate and caloric content for several commercially available feeding fluids, which may be utilized in accordance with one or more aspects of the invention.

At Table 1, the calculated flow rates relative to viscosity for each of the fluids are listed; and FIG. 7A graphically presents the results. Averages of the calculated, measured feeding rates are also listed and graphically presented at FIG. 8A. At Table 2, the calculated flow rates relative to caloric content for each of the fluids are listed; and FIG. 7B graphically presents the results. Averages of the calculated, measured feeding rates are also listed and graphically presented at FIG. 8B.

TABLE 1

Measured Flow Rate Relative to Viscosity.

|  | Feeding Set 1 mL/hr | Feeding Set 2 mL/hr | Feeding Set 3 mL/hr | Average Feeding Rate mL/hr | Viscosity cP |
|---|---|---|---|---|---|
| Tap water | 120.0 | 125.1 | 127.4 | 124.2 | 1 |
| JEVITY ® 1 Cal | 119.8 | 121.4 | 119.5 | 119.8 | 75 |
| PROMOTE ® WITH FIBER | 118.9 | 117.0 | 120.1 | 118.7 | 78 |
| TWOCAL ® HN | 116.3 | 119.0 | 122.5 | 119.3 | 93 |

TABLE 2

Measured Flow Rate Relative to Caloric Content.

|  | Feeding Set 1 mL/hr | Feeding Set 2 mL/hr | Feeding Set 3 mL/hr | Feeding Set 4 mL/hr | Average Feeding Rate mL/hr | Caloric Content cal/mL* |
|---|---|---|---|---|---|---|
| Tap water | 126.5 | 125.9 | 120.9 | 124.9 | 124.5 | — |
| JEVITY ® 1 Cal | 117.3 | 119.6 | 115.2 | 120.0 | 118.0 | 1,060 |
| JEVITY ® 1.2 Cal | 119.2 | 121.6 | 116.9 | 122.2 | 120.0 | 1,200 |
| JEVITY ® 1.5 Cal | 116.6 | 119.6 | 114.4 | 119.2 | 117.4 | 1,500 |
| TWOCAL ® HN | 114.7 | 117.4 | 112.5 | 118.6 | 115.8 | 2,000 |

*As indicated on the respective labels of each of these fluids

The measured corresponding flow rate for each of JEVITY® 1 CAL, JEVITY® 1.2 CAL, JEVITY® 1.5 CAL, PROMOTE® WITH FIBER, and TWOCAL® HN formulae can then be stored in the memory of the flow control apparatus and be utilized to determine respective correlation factors for each of the feeding fluids, and each of the corresponding correlation factors can be retrieved by the controller for future feeding operations to modify the user-selected feeding rate and determine a flow rate that compensates based on viscosity, caloric content, or both. For example, a correlation factor for the TWOCAL® HN formula of 1.08 (=125/115.8) can be used to modify a user-defined feeding rate to operate the pump at the modified flow rate.

Figure 8A:
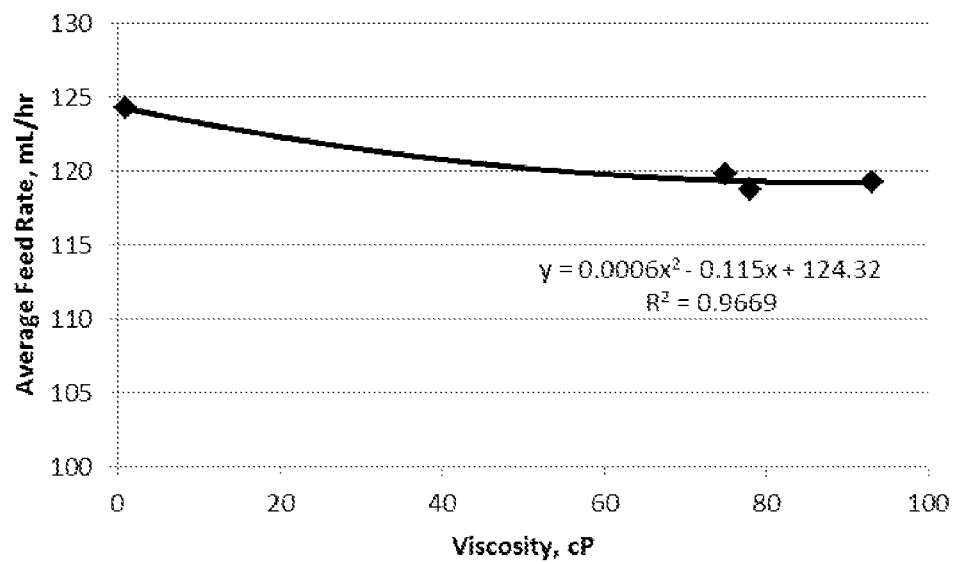
FIG. 8A is a graph illustrating an associated trend line of average feeding fluid flow rate relative to viscosity for the several commercially available feeding fluids presented in FIG. 7A, and the second order polynomial equation and $R^2$ of the associated trend line.
Figure 8B:
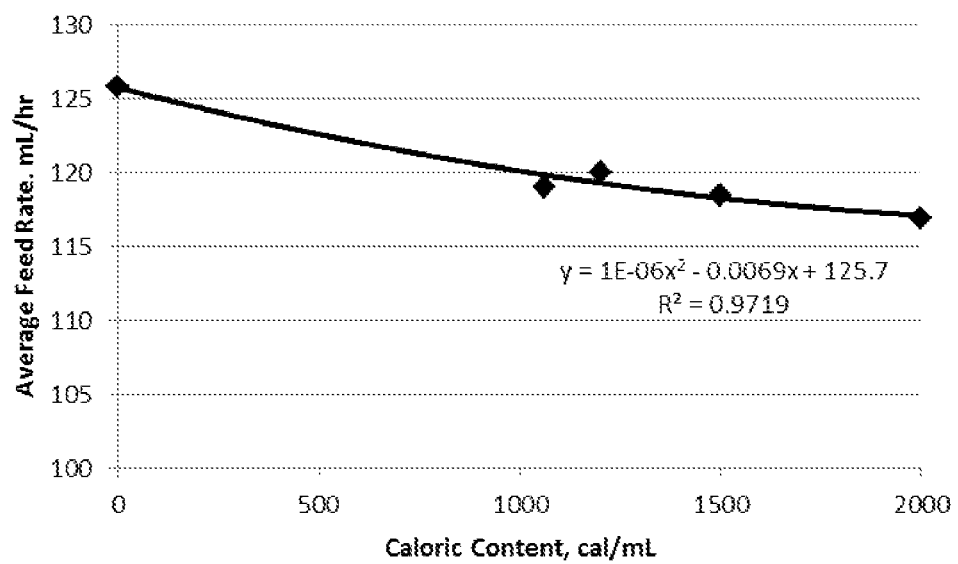
FIG. 8B is a graph illustrating an associated trend line of average feeding fluid flow rate relative to caloric content for the several commercially available feeding fluids presented in FIG. 7B, and the second order polynomial equation and $R^2$ of the associated trend line.

FIGS. 8A and 8B graphically illustrate the average flow rate through the feeding sets for each of the feeding fluids in Tables 1 and 2, respectively. The second order polynomial relationship of the trend lines is also presented. Thus, further aspects of the invention can utilize the relationship, based on viscosity or caloric content, or both, to determine an operating flow rate to achieve the user-selected feeding rate.

Having now described some illustrative embodiments and aspects of the invention, the foregoing is merely illustrative and not limiting, having been presented by way of example only. Moreover, the invention is directed to each feature, system, subsystem, or technique described herein and any combination of two or more features, systems, subsystems, or techniques described herein, if such features, systems, subsystems, and techniques are not mutually inconsistent, is considered to be within the scope of the invention as embodied in the claims. In particular, although many of the examples presented herein involve specific combinations of method acts or system elements, those acts and those elements may be combined in other ways. Thus, acts, elements, and features discussed only in connection with one embodiment are not intended to be excluded from a similar role in other embodiments. Further, the parameters and configurations described herein are exemplary and that actual parameters and/or configurations will depend on the specific application in which the systems and techniques of the invention are used. For example, it is to be understood that one or more aspects of the present invention can be applied to fluid pumps generally; and multiple display screens may be used in conjunction with a display to assist a user to select an enteral feeding fluid. Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

All publications, patents, and patent documents referred to in this document are incorporated by reference herein in their entirety, as though individually incorporated by reference. In the event of inconsistent usages between this document and those documents so incorporated by reference, the usage in any the incorporated references should be considered supplementary to that of this document; for irreconcilable inconsistencies, the usage in this document controls.

When introducing elements of aspects of the invention or the embodiments thereof, the articles "a," "an," "the," and "said" are intended to mean that there are one or more of the elements. The terms "comprising," "including," "carrying," "having," "containing," and "involving" are open-ended terms to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Ordinal terms such as "first," "second," and "third" in the claims to modify a claim element do not by itself connote any priority, precedence, or order of one claim element over another or the temporal order in which acts of a method are performed, but are used merely as labels to distinguish one claim element having a certain name from another element having a same name, but for use of the ordinal term, to distinguish the claim elements.

The following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72(b) to allow the reader to quickly ascertain the nature of the technical disclosure. It is submitted with the understanding that it will not be used to interpret or limit the scope or meaning of the claims.

The invention claimed is:
1. An enteral fluid delivery system, comprising:
a pump having a motor coupled to a rotor, the rotor configured to accept a portion of tubing, the motor configured to drive the rotor to compress the tubing for delivering an enteral feeding fluid to a patient during a feeding cycle;
a memory storing at least one characteristic representative of a plurality of types of enteral feeding fluids;

a user interface operatively connected to the memory, the user interface enabling a user to select at least one of the types of enteral feeding fluids; and a processor operatively connected to the pump, the processor being configured to provide a flow rate of the pump to deliver the selected enteral feeding fluid based on the at least one characteristic of the selected enteral feeding fluid, wherein the processor is further configured to retrieve predetermined flow correlation data from the memory and to adjust the flow rate by altering a rotational speed of the motor based on the retrieved predetermined flow correlation data stored in the memory, the predetermined flow correlation data stored in the memory corresponding to a viscosity of the selected enteral feeding fluid, and the predetermined flow correlation data comprising a ratio of a user-defined feeding rate to an average feeding rate of the selected enteral feeding fluid relative to the viscosity thereof.

2. The system of claim 1, wherein the processor is further configured to adjust a selected feeding rate to provide the flow rate based on the viscosity of the selected enteral feeding fluid.

3. The system of claim 1, wherein the processor is configured to provide the flow rate based on at least one of a low viscosity of less than about 75 cP and a high viscosity of greater than or equal to about 75 cP.

4. The system of claim 3, wherein the processor is configured to increase a selected feeding rate and provide the flow rate for a low viscosity enteral feeding fluid.

5. The system of claim 1, wherein the processor is configured to adjust a selected feeding rate and provide the flow rate based on a patient's specific patient group, wherein the patient group comprises at least one of an infant and an elderly adult.

6. The system of claim 1, wherein the processor is configured to adjust a selected feeding rate to provide the flow rate based on a caloric content of the selected enteral feeding fluid as the at least one characteristic.

7. The system of claim 6, wherein the processor is configured to decrease the selected feeding rate for a caloric content enteral feeding fluid having more than approximately 1500 cal/mL.

8. The system of claim 6, wherein the processor is further configured to increase the selected feeding rate for a caloric content enteral fluid having less than 1500 cal/mL.

9. The system of claim 1, wherein the predetermined flow correlation data further corresponds to at least one of an osmolality, a digestibility, a caloric content, a protein content, a sugar content, a fat content, a fiber content, a free water content, a carbohydrate content, a cholesterol content, an amino acid content, a vitamin content, a mineral content, a nitrogen content, a sodium content, a potassium content, a chloride content, a calcium content, a magnesium content, an electrolyte content, and a nutritional requirement.

10. An enteral fluid delivery system, comprising:

a pump, wherein the pump comprises a motor coupled to a rotor, wherein the rotor is configured to receive a portion of a tube, and wherein the motor is configured to drive the rotor to compress the tube for delivering an enteral fluid to a patient;

a memory device configured to store at least an identifier and a viscosity of each of a plurality of enteral fluids;

a user interface coupled to the memory device, wherein the user interface is configured to enable selection of the identifier of one enteral fluid of the plurality of enteral fluids;

a processor coupled to the memory device and the user interface, wherein the processor is configured to provide an initial flow rate of the pump to deliver the selected enteral fluid, wherein the processor is further configured to provide an adjusted flow rate of the pump to adjust the initial flow rate based on predetermined flow correlation data stored in the memory device, wherein the predetermined flow correlation data corresponds to the viscosity of the selected enteral fluid stored in the memory device, and wherein the predetermined flow correlation data comprises a ratio of a user-defined feeding rate to an average feeding rate of the selected enteral fluid relative to the viscosity thereof; and a pump control circuit coupled to the processor and the pump, wherein the pump control circuit is configured to energize the pump motor at a first rotational speed corresponding to the initial flow rate provided thereto by the processor and a second rotational speed corresponding to the adjusted flow rate provided thereto by the processor.

11. The system of claim 10, wherein the processor is configured to provide the adjusted flow rate to adjust the initial flow rate based on a caloric content of the selected enteral feeding fluid.

12. The system of claim 10, wherein the adjusted flow rate is greater than the initial flow rate when the ratio is greater than 1.00.

13. The system of claim 10, wherein the adjusted flow rate is less than the initial flow rate when the ratio is less than 1.00.

* * * * *